United States Patent [19]

Papenfuhs et al.

[11] 4,281,187

[45] Jul. 28, 1981

[54] PROCESS FOR THE PREPARATION OF 2,4-DINITROPHENYL UREA

[75] Inventors: Theodor Papenfuhs, Frankfurt am Main; Kurt Gengnagel, Kriftel, both of Fed. Rep. of Germany

[73] Assignee: Hoechst Aktiengesellschaft, Frankfurt am Main, Fed. Rep. of Germany

[21] Appl. No.: 105,561

[22] Filed: Dec. 20, 1979

[30] Foreign Application Priority Data

Dec. 23, 1978 [DE] Fed. Rep. of Germany ....... 2855882

[51] Int. Cl.$^3$ .......................................... C07C 126/04
[52] U.S. Cl. ................................................... 564/50
[58] Field of Search ...................... 260/553 A; 564/50

[56] References Cited

U.S. PATENT DOCUMENTS

| 2,826,611 | 3/1958 | Fischback et al. | 260/553 A |
| 3,119,867 | 1/1964 | Lecher et al. | 260/553 A |

FOREIGN PATENT DOCUMENTS 1045170 10/1966 United Kingdom ................ 260/553 A

OTHER PUBLICATIONS

J. Prakt. Chemie 110, pp. 300–301, (1925).

*Primary Examiner*—Thomas A. Waltz
*Attorney, Agent, or Firm*—Curtis, Morris & Safford

[57] ABSTRACT

2,4-Dinitrophenyl urea is obtained in a technologically simple manner with high yield, if 2,4-dinitro-1-chlorobenzene is reacted with cyanamide, advantageously in an excess amount, at a temperature at from about 55° to 75° C. to yield 2,4-dinitrophenyl cyanamide which is subsequently hydrolyzed without intermediate isolation in an aqueous acid medium at a temperature of from about 40° to 75° C. 2,4-Dinitrophenyl urea serves as starting compound for the preparation of 5-amino-benzimidazolones which may be employed, for example, when preparing azo compounds.

5 Claims, No Drawings

PROCESS FOR THE PREPARATION OF 2,4-DINITROPHENYL UREA

It is a well-known fact that the reaction of 2,4-dinitro-1-chlorobenzene with cyanamide in ethanol yields 2,4-dinitrophenyl cyanamide which after its isolation can be converted into 2,4-dinitrophenyl urea by heating with alcoholic hydrochlorid acid (cf. J. pr. Ch. 110, 300+301, (1925)). A process of this kind is not suitable for being performed on an industrial scale, since the organic solvent must be recovered for ecological reasons.

It has now been found that 2,4-dinitrophenyl urea can be obtained in a technologically simple manner in the reaction of 2,4-dinitro-1-chlorobenzene with cyanamide with subsequent acid hydrolysis of the 2,4-dinitrophenyl cyanamide, if this reaction of the 2,4-dinitro-1-chlorobenzene with the cyanamide and the subsequent hydrolysis are effected in an aqueous medium and without intermediate isolation of the 2,4-dinitrophenyl cyanamide.

Thus, the present invention provides an improved process for the preparation of 2,4-dinitrophenyl urea by a reaction of 2,4-dinitro-1-chlorobenzene with cyanamide and subsequent acid hydrolysis of the 2,4-dinitrophenyl cyanamide, which improvement comprises carrying out the reaction of the 2,4-dinitro-1-chlorobenzene with the cyanamide and the subsequent hydrolysis in an aqueous medium and without intermediate isolation of the 2,4-dinitrophenyl cyanamide. The reaction with the cyanamide is advantageously carried out at a temperature of from 55° to 75° C., and the subsequent hydrolysis at a temperature of from 40° to 75° C.

More specifically, the process of the invention may be carried out, for example, according to the following method: The 2,4-dinitro-1-chlorobenzene is introduced into water, while preferably using from 2 to 5 times its weight of water; thereafter an excess amount of cyanamide is added and an aqueous solution of an alkali metal hydroxide (such as of sodium or potassium hydroxide, and/or of an alkali metal salt of a weak acid, such as of sodium carbonate) is added in an amount approximately equivalent to that of the cyanamide. This reaction mixture is subsequently heated to about 60° to 65° C., at which point the reaction starts; the temperature is allowed to rise to about 70° to 75° C., with cooling, if required. Upon reaching this temperature, the reaction is continued at about 60 to 65° C., while stirring; the reaction period should be in the range of from about 4 to 5 hours. Thereafter the reaction mixture is introduced, while stirring, into an aqueous hydrochloric acid of about 30% strength, the amount of which being such that the reaction mixture is rendered strongly acidic. The temperature applied should not exceed about 70° C. The acid solution is then stirred again at a temperature of from about 70° to 75° C. for several hours, approximately 5 to 6 hours, and then cooled to a temperature of less than 10° C., especially to a temperature of from 3° to 5° C. At this low temperature, the 2,4-dinitrophenyl urea formed separates; in order to maximize the amount obtained of this final substance the separation process is advantageously performed at the said temperature for one hour, while stirring. The 2,4-dinitrophenyl urea may then be filtered off by suction and dried at about 60° C. It is obtained in a high yield and purity.

In order to ensure a complete conversion in the reaction, the cyanamide is employed in an excess amount, preferably in a molar amount of 1.5 to 2.5, especially 1.8 to 2.3, calculated on the 2,4-dinitro-1-chlorobenzene. The alkali metal serves to dissolve the cyanamide and is therefore employed in about 1 to 1.2 times the equivalent amount, calculated on the cyanamide.

2,4-Dinitrophenyl urea is already well-known. It may serve, for example, as starting compound for the preparation of 5-aminobenzimidazolone, e.g. in the process for the preparation of azo compounds as diazo component, for example cf. German Offenlegungsschrift No. 15 44 394. 5-Aminobenzimidazolone is obtained from 2,4-dinitrophenyl urea by catalytic reduction of the nitro groups and cyclization, while splitting off ammonia, in accordance with another invention, i.e. U.S. Patent Application Ser. No. 105,500 (internal reference: HOE 78/F 285) filed concurrently herewith and corresponding to the German Convention Application No. P 28 883.0 of Dec. 23, 1978. Furthermore, it is known to use 2,4-dinitrophenyl urea in animal feeds for controlling intestinal parasites according to U.S. Pat. No. 2,826,611.

The following Example serves to illustrate the process of the invention. The parts are parts by weight, the percentages are percent by weight, unless otherwise stated.

EXAMPLE

200 Parts of 2,4-dinitro-1-chlorobenzene are introduced into 600 parts of water of 50° to 55° C. After the addition of 160 parts of an aqueous 50% cyanamide solution, 229 parts of an aqueous 33% sodium hydroxide solution and 40 parts of anhydrous sodium carbonate possibly being dissolved in 100 parts of water, the reaction mixture thus prepared is heated to 60° to 65° C. After this temperature has been reached, the reaction sets in slowly. The reaction temperature is allowed to rise to about 70° to 75° C. without further heating, if necessary while cooling, and said temperature range is maintained, whereupon the reaction is completed within about 5 hours at 60° to 65° C., while stirring, with a temperature drop and with external heating.

Subsequently the warm alkaline suspension is introduced into a mixture of 1400 parts of an aqueous 30% hydrochloric acid and 300 parts of water of 60° to 70° C. The reaction mixture is heated to 70° to 75° C., stirring is continued at this temperature for 6 hours, thereafter the mixture is cooled to 3°–5° C., whereupon it is continued to be stirred for another hour at said temperature. The 2,4-dinitrophenyl urea having precipitated is filtered off with suction, suction-dried and washed with 1500 parts of cold water, then again suction-dried and dried in the circulating air drier at 60° C.

There are obtained 213 parts (corresponding to 95.4% of the theory) of 2,4-dinitrophenyl urea having a melting point from 197° to 199° C.

What is claimed is:

1. In a process for the preparation of 2,4-dinitrophenyl urea comprising a reaction of 2,4-dinitro-1-chlorobenzene with cyanamide and subsequent acid hydrolysis of the 2,4-dinitrophenyl cyanamide, the improvement consisting of conducting the reaction of the 2,4-dinitro-1-chlorobenzene with the cyanamide and the subsequent acid hydrolysis in an aqueous medium without intermediate isolation of the 2,4-dinitrophenyl cyanamide.

2. A process according to claim 1, in which the reaction with the cyanamide is carried out at a temperature of from 55° to 75° C.

3. A process according to claim 1 or 2, in which the acid hydrolysis is carried out at a temperature of from 40° to 75° C.

4. A process according to claim 1 or 2, in which a molar amount of 1.5 to 2.5 of cyanamide, calculated on the amount of 2,4-dinitro-1-chlorobenzene, is used during the reaction.

5. A process according to claim 3, in which a molar amount of 1.5 to 2.5 of cyanamide, calculated on the amount of 2,4-dinitro-1-chlorobenzene, is used during the reaction.

* * * * *